(12) United States Patent  
Stockdale et al.

(10) Patent No.: US 7,821,270 B2
(45) Date of Patent: Oct. 26, 2010

(54) ELECTRODE CONTACT PELLET AND ASSOCIATED PHOTOIONISATION DETECTOR ASSEMBLY

(75) Inventors: Mark Julian Stockdale, Harston (GB); Kara Michele Eagling, Royston (GB)

(73) Assignee: Ion Science Limited, Cambridge (GB)

( * ) Notice: Subject to any disclaimer, the term of this patent is extended or adjusted under 35 U.S.C. 154(b) by 365 days.

(21) Appl. No.: 12/119,644

(22) Filed: May 13, 2008

(65) Prior Publication Data

US 2009/0115423 A1    May 7, 2009

(30) Foreign Application Priority Data

May 30, 2007   (GB)   ................. 0710287.4

(51) Int. Cl.
*G01N 27/62*   (2006.01)
(52) U.S. Cl. ............... 324/459; 439/9; 439/12; 439/45; 439/111; 439/116
(58) Field of Classification Search ........... 324/459; 439/9, 12, 45, 111, 116
See application file for complete search history.

(56) References Cited

U.S. PATENT DOCUMENTS

| 4,413,872 | A |   | 11/1983 | Rudy, Jr. et al. |
| 5,352,995 | A | * | 10/1994 | Mouissie ............ 333/181 |
| 5,571,026 | A | * | 11/1996 | Kahre ................ 439/242 |
| 5,959,394 | A |   | 9/1999  | Lin |
| 6,129,559 | A | * | 10/2000 | Hirata et al. ......... 439/74 |
| 6,320,388 | B1| * | 11/2001 | Sun et al. ........... 324/464 |
| 7,046,012 | B2| * | 5/2006  | Dean et al. ......... 324/459 |
| 7,101,232 | B2| * | 9/2006  | Shimizu ............. 439/731 |
| 2001/0002343 | A1 | * | 5/2001 | Suzuki .............. 439/101 |
| 2003/0027449 | A1 | * | 2/2003 | Roberts et al. ...... 439/329 |
| 2005/0242293 | A1 | * | 11/2005| Benveniste ......... 250/396 R |
| 2007/0218713 | A1 | * | 9/2007 | Kato ................. 439/67 |

FOREIGN PATENT DOCUMENTS

JP       2001028282       1/2001

* cited by examiner

*Primary Examiner*—Timothy J Dole
*Assistant Examiner*—Benjamin M Baldridge
(74) *Attorney, Agent, or Firm*—Chernoff, Vilhauer, McClung & Stenzel LLP (57)   ABSTRACT

A demountable pellet is disclosed for use as an electrode contact assembly. The pellet comprises a base 1 upon which is mounted a plurality of electrodes 18, 19, 20 arranged in respective spaced parallel planes and having respective contacts 23, 24, 25 protruding from them. A closure 2 for the base 1 has a member 11, 12, 13 engaging at least one of the electrode contacts. In an unassembled condition of the pellet, with the closure 2 separate from the base 1 and each closure member disengaged from its respective electrode contact, the contacts 23, 24, 25 lie in respective spaced parallel planes. In the assembled condition of the pellet with each closure member engaging its respective electrode contact, at least one of the contacts 23, 24, 25 lies in a plane other than that in which it lay in the unassembled condition of the pellet.

16 Claims, 7 Drawing Sheets

ELECTRODE CONTACT PELLET AND ASSOCIATED PHOTOIONISATION DETECTOR ASSEMBLY

FIELD OF THE INVENTION

This invention relates to a demountable electrode contact assembly. Such self-contained sub-assemblies are conveniently referred to as "pellets". The present invention is particularly suitable for use in a photoionisation detector (PID) which enables gases, particularly air, to be sampled for gases which form ions when exposed to light emitted from a UV light source within the PID. These photoionisable gases can be harmful or dangerous to health, can present a fire risk, and/or can indicate the failure of equipment designed to contain them in a gaseous or liquid state.

BACKGROUND OF THE INVENTION

PIDs usually incorporate a chamber through which a sample gas is passed by means of suitable tubing, pumps, fans and the like. The chamber is exposed to photons. A proportion of the photons has sufficient energy to disassociate any photoionisable gas molecules within the sample into ions. This process is known as photoionisation and the chamber itself is described as a photoionisation chamber. Each photoionisation event engages one photon and causes equal numbers of positively and negatively charged ions to form, usually one of each. An electric field is applied across the chamber by means of two or more electrodes which are a part of, or are contained within, the chamber walls. The ions are attracted to the electrodes, causing a current to flow between the two or more electrodes within the chamber. This current is amplified and displayed, providing an indication of the presence of the target gas molecules.

PIDs also incorporate means to produce UV light of sufficient energy to ionise gases of interest, such as volatile organic carbon compounds, without ionising common constituents of clean air, such as nitrogen, oxygen, argon and/or carbon dioxide. UV discharge electrodeless lamps of up to a few centimeters length and up to about one centimeter diameter are commercially available. These lamps contain a gas at a few millibars of pressure, typically a noble gas such as krypton. Soda glass is a suitable material for the body of the lamps, terminating at one end with a wall which typically comprises a flat round disc of magnesium fluoride and lithium fluoride which are transparent to photons in the energy range of interest and which typically forms one wall of the ionisation chamber.

It is desirable to remove and thereby detect photogenerated ions in a photoionisation chamber by means of electrodes located no more than a millimeter or two from the lamp face and from each other. The reasons for this are fourfold. First, photoionising UV light may be adsorbed not only by photoionisable gases but also by other gaseous constituents of air, most significantly, moisture. Thus an electrode network extending more than one or two millimeters from the lamp face gives rise too readily to a response to ionisable gas within air which varies with humidity. Second, the absorption of light by ionisable gases increases with distance from the lamp, causing the response to an organic gas not to increase in proportion to its concentration, even at quite modest concentrations (tens of parts per million of ionisable gas) in chambers having an electrode gap of more than a few millimeters. Third, a few hundred volts per mm of electrode gap must be applied between the electrodes in order to strip out all the photo-ions between the electrodes before they are conveyed by sample flow away from the electrodes or recombine to form neutral molecules which are not attracted to the electrodes and do not contribute to the photoionisation current. Generating such a voltage becomes more problematic as the gap across the electrodes is increased. Finally, positive and negative ions are more likely to encounter each other and recombine as the electrode gap is increased, again causing poor proportionality between response and ionisable gas concentration.

The electrodes are typically of planar form and have thicknesses less than a few tenths of a millimeter. One electrode, namely the anode, is at a positive electric potential relative to the other electrode, namely the cathode, and abuts or is otherwise located very close to the lamp window, attracting negatively-charged ions. The anode includes means for admitting light through it, for example, by slots or holes. The cathode is at a negative potential relative to the anode and is placed parallel to, and within a millimeter of, the anode attracting positively-charged ions. This arrangement assures that positive ions, which form more contaminating products than do negative ions, are conveyed away from the lamp window.

However, some ionisable gases form negatively charged ions which are attracted towards the lamp windows and, are adsorbed thereon. Further, collisions between such negative ions and neutral molecules within the ionisation chamber can generate ion clusters which, being of high molecular weight, are very prone to deposition on surfaces, such as the lamp window. Further, the sample gas might contain non-volatile material in aerosol form which can also deposit on the lamp window. In short, the lamp window can be fouled by species within the sampled air, whereby the sensitivity of the PID to a given concentration of ionisable species is reduced. Most ionisable gases are organic and, therefore, it is reasonable to anticipate that window fouling is usually caused by a film of organic material. Sometimes, a photoionisation chamber may also be fouled by liquids being drawn into it.

It will be apparent that photoionisation chambers are frequently of small dimensions and, in certain applications, prone to contamination or mechanical damage during use and servicing. It is thus desirable to design the photoionisation chamber to be readily replaceable. Such replaceable chambers will include electrical terminals to the photoionisation electrodes described above. Other gas sensing ionisation chambers might also be advantageously rendered easily replaceable for similar reasons.

However, there has frequently been difficulty in assuring good electrical contact between the electrode terminals in the replaceable chamber and terminals from supporting electronic circuitry contained within a sensing member which accommodates the replaceable ionisation chamber. In particular, spring-loaded retractable pins, which ensure a force is applied between the contacts, do not always retain their spring loading. Also, pins inserted into metal or metal-coated holes are prone to failure after multiple engagement and removal of the ionisation chamber.

The invention seeks to mitigate the problems and disadvantages associated with the known electrical contacts of disposable PID electrode assemblies discussed above.

Needs dictate that the small detector pellets of such assemblies have five external connections located within close proximity of each other, to allow the working electrodes, as previously described, maximum space to collect the charged ions in the operating chamber part of the detector pellet. Five connections from an external printed circuit board (PCB) to the respective connections located on this pellet have to be constructed in such a manner that manufacturing tolerances in contact alignment in three dimensions are readily overcome.

One form of prior art arrangement uses spring-loaded telescopic pins which can change their length to take up manufacturing tolerances in one dimension and are designed so they depress further to provide firm contact on preformed metal contacts located within the pellet against spring pins. They rely upon an internal, suitably small, coil spring located within the assembly. This technique requires much space and if specialised miniature telescopic pins are used, then the costs may be prohibitive.

Preformed contact surfaces in the pellet may be used to bring all the differently placed electrode contacts on to one common plane for the spring-loaded telescopic pins to press upon.

There are several technical problems with this approach.

First, the expensive telescopic pins are, for practical reasons, located within the retained PCB exterior to the disposable pellet. The whole assembly can be used in aggressive and potentially corrosive atmospheres and thus, after some repeated use, the pins may become damaged or corroded, thereby losing their effectiveness in communicating electrical signals between the pellet and the externally retained PCB. The prior art arrangements make no allowances for this and thus disposal of the pellet together with the whole externally retained PCB must be effected.

A further problem with this prior art arrangement is at the points of contact between the pins and contacts.

These points of contact are generally between the pins and contacts which are perpendicular to each other and, thus, have no means for wiping the points of contact clean whilst making contact between the pins and contacts. Oxide or external debris if not wiped away during the contact-making generation may impair good ohmic contact for electrical signals.

Another prior art arrangement employs a pin and slide socket arrangement. The pin is located within the electrode pellet parallel to the direction of pellet placement with respect to the mounting PCB and slides into a suitably placed socket located on the PCB. This has the advantage of being slightly less expensive than the prior art arrangement discussed above and the barrel action of the interference spring connection within the socket allows the slide sockets to be packed more tightly together.

Advantages of this prior art arrangement over the previous one described above will now be explained.

First, there is a wiping action while contact is being made which aids oxide and debris removal and, hence, enhances ohmic contact.

Second, provided the socket is long enough in its sliding contact length, then a common pin may be connected to the differently placed grids, thus relying upon the comparatively long travel of contact engagement to take up both manufacturing tolerances and electrode grid position.

However, this particular prior art arrangement does have some disadvantages.

The main disadvantage is that the socket and pins must be parallel to each other and to the direction of their relative travel. Clearly, this is not too much of a problem if it is just one or two pins, as in the prior art example, but when, say, five pins are used then this becomes more difficult to achieve. Further, this option still tends to be unduly expensive in relation to unit costs and assembly requirements.

OBJECT OF THE INVENTION

It is an object of the present invention to provide a pellet, and an associated method of its assembly, for use as an electrode contact assembly in a PID which overcomes, or at least substantially reduces, the disadvantages discussed above in relation to the prior art arrangements. For example, the pellet can be low cost and therefore readily replaceable.

SUMMARY OF THE INVENTION

Accordingly, one aspect of the invention resides in a demountable pellet for use as an electrode contact assembly, comprising a base upon which is mounted a plurality of electrodes arranged in respective spaced parallel planes and having respective contacts protruding therefrom, and a closure for the base having a member engaging at least one of the electrode contacts, wherein, in an unassembled condition of the pellet, with the closure separate from the base and the at least one closure member disengaged from its respective electrode contact, the contacts lie in respective spaced parallel planes and wherein, in the assembled condition of the pellet with the at least one closure member engaging its respective electrode contact, at least one of the contacts lies in a plane other than that in which it lay in the unassembled condition of the pellet.

Advantageously, the closure member(s) are protrusions from the closure but other means, such as the shape of the closure, can readily be employed for engaging the electrode contact(s) and thereby changing the plane thereof when the pellet is in an assembled condition.

In an embodiment of the pellet to be described hereinbelow, the pellet base has three electrodes mounted to it, with three corresponding electrode contacts lying in respective, spaced parallel electrode planes when the pellet is in its unassembled condition. When the closure is fitted to the base, closure members engage their respective contacts and deform two of them into the same plane as the third contact.

The pellet base may be provided in one wall thereof with a plurality of holes corresponding to the number of electrode contacts, so that, in the assembled condition of the pellet, the contacts overlie respective ones of those holes through which fixed terminal pins, preferably of the same height, can be received to engage respective ones of the contacts, to provide ohmic contacts therebetween. As the fixed terminal pins are received through the base holes, they may deform the contacts in scraping engagement therewith, to enhance such ohmic contacts. In this embodiment, the free ends of the contacts, which are spaced from the closure members engaging them, are deformed in a direction which is generally opposite to that in which the contacts are deformed initially when the closure is fitted to the base.

A second aspect of the invention is directed to a method of assembling a pellet for use as a demountable electrode contact assembly, which method comprises providing a base upon which is mounted a plurality of electrodes arranged in respective spaced parallel planes and having respective contacts which protrude therefrom and lie in respective spaced parallel planes; providing a closure having at least one member for engaging one or more of the electrode contacts when the closure is fitted to the base; and fitting the closure to the base, to cause the at least one closure member to engage its electrode contact and to deform the said electrode contact into a plane other than that in which it lay prior to the closure being fitted to the base.

In the embodiment mentioned above and to be described in more detail hereinbelow, three electrode contacts are provided and, in the assembled condition of the capsule, all three contacts lie in a common plane, preferably overlying respective holes through which fixed terminal pins, preferably of the same height, are receivable from the exterior of the pellet.

Such terminal pins, when received through their respective holes in the base of the pellet, deform their corresponding electrode contacts in a direction generally opposite to that of the initial deformation of the contacts when the capsule is assembled.

The fixed terminal pins may be those of a PID capsule, in which case, a further aspect of the invention resides in an assembly comprising a PID capsule to which is fitted, preferably detachably, a pellet in accordance with the invention and as defined and described above, wherein the terminal pins of the PID capsule engage respective ones of the electrode contacts in ohmic contact therewith.

BRIEF DESCRIPTION OF THE DRAWINGS

The invention will now be described further, by way of example, with reference to the accompanying drawings, in which.

DETAILED DESCRIPTION OF THE PREFERRED EMBODIMENTS

All references to downward and other directions are relative to the base of the pellet, as shown in the drawings, and do not imply any particular orientation of the pellet.

Figure 1:
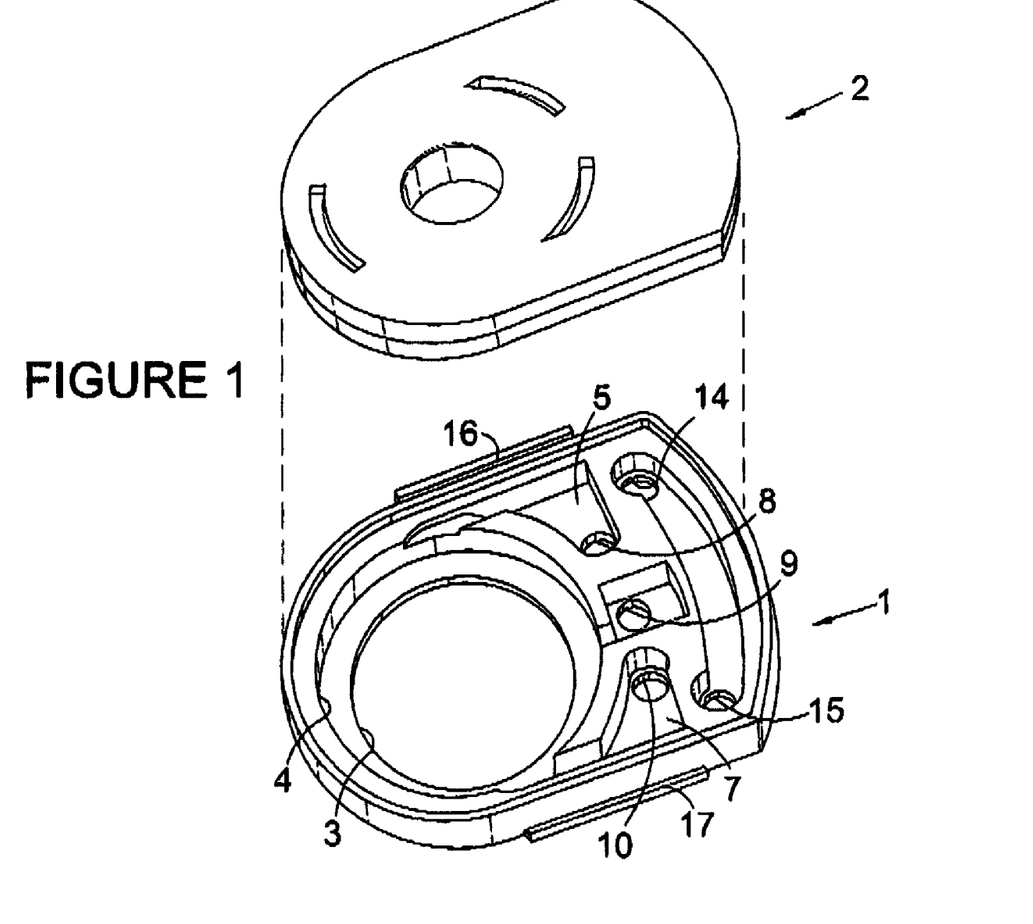
FIG. 1 is an exploded perspective view of a partially-assembled electrode pellet with a moulded base body and lid.

Referring first to FIG. 1 of the accompanying drawings, an electrode pellet in accordance with the invention, and for use with a photoionisation detector (PID) capsule, comprises a moulded plastics base body, generally designated 1, and a moulded plastics lid, generally designated 2, which can be fitted and secured to the pellet base body 1.

The base body 1 comprises a circular aperture 3 for alignment with one end of an ionisation lamp of a PID capsule, as will be described hereinbelow.

A circular recess 4 concentric with the aperture 3 is arranged to receive therein three electrodes (not shown) separated by respective electrically-insulating spacers (also not shown), as will also be described hereinbelow.

Each electrode has a contact (not shown) which extends into a respective one of three recesses 5, 6, 7 in the base body 1, to overlie a respective one of three holes 8, 9, extending through the base body 1 from the recesses 5, 6, 7. Those three electrode contacts lie in spaced parallel planes within the base body 1.

Figure 2:
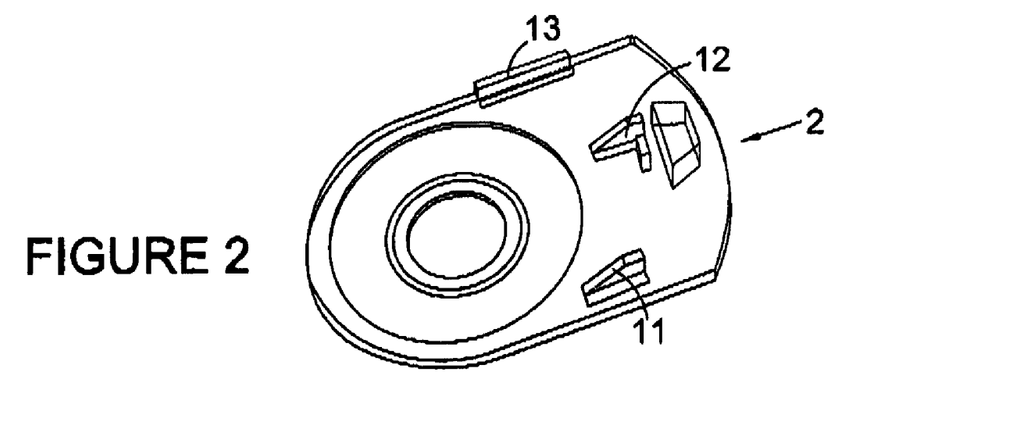
FIG. 2 is a perspective view of the underside of the lid of the pellet.

Referring now to FIG. 2 of the accompanying drawings, the underside of the pellet lid 2 comprises three protrusions 11, 12, 13 which, when the lid 2 is fitted to the base body 1 with the electrodes and associated contacts in place, engage respective contacts to deform them into a common plane within the base body 1, while still overlying respective holes 8, 9, 10.

This arrangement is such that the protrusions 11, 12, 13 of the lid 2 are spaced from the respective holes 8,9,10, with the free ends of the electrode contacts still overlying the respective holes 8, 9, 10.

As will be described hereinafter, the holes 8, 9, 10 are arranged to receive therethrough fixed terminal pins of equal height of a PID capsule.

Figure 3:
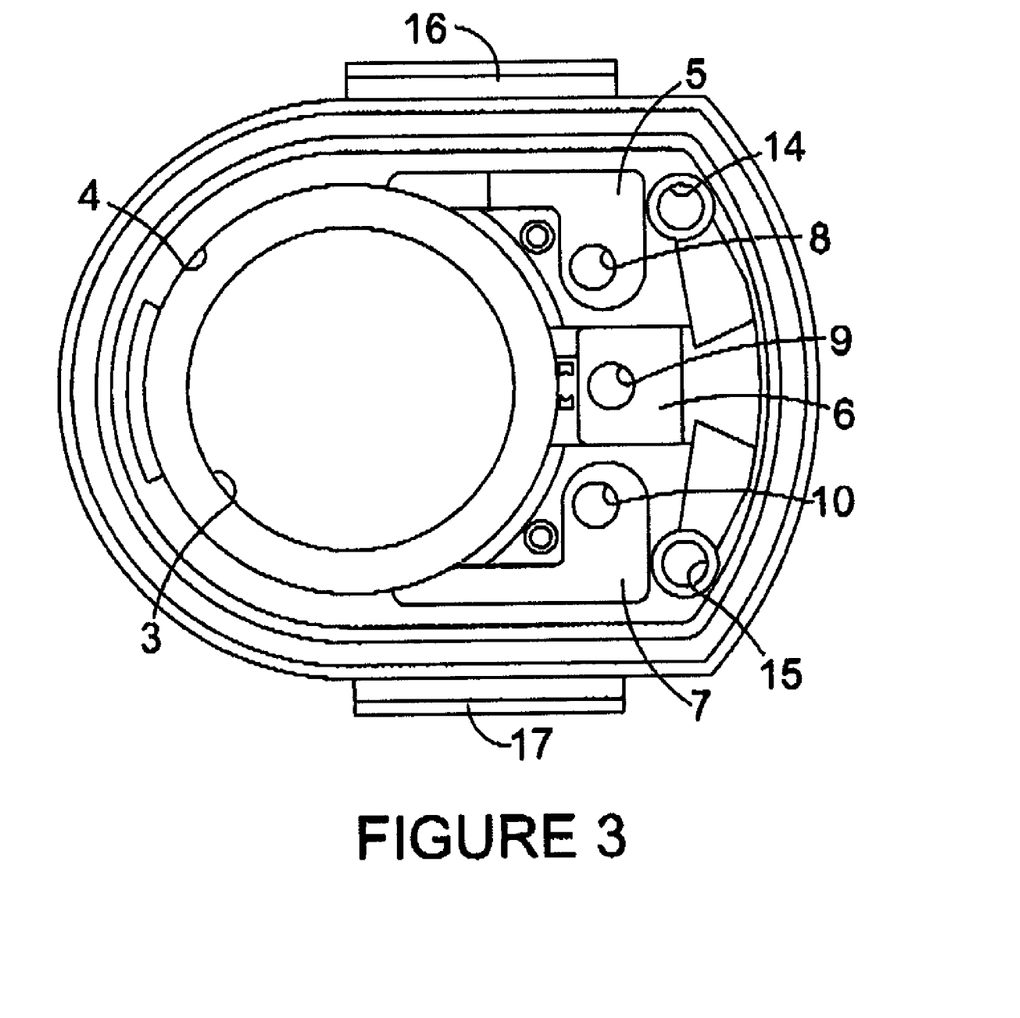
FIG. 3 is a plan view of a base body of the pellet similar to that shown in FIG. 1.

In FIG. 3 of the drawings, there is shown a more detailed plan view of the base body 1, illustrating the circular aperture 3, circular recess 4, recesses 5, 6, 7 for receiving the electrode contacts and the respective terminal pin-receiving holes 8, 9, 10.

The base body 1 is also provided with two further holes 14, 15 through which are receivable two further terminal pins for contacting a contact strip (also not shown) extending between the holes 14, 15 as part of a circuit for determining the presence of the pellet when associated with a PID capsule.

Two opposed sides of the base body 1 are provided with respective elongate lugs 16, 17 which provide a snap-fit of the assembled pellet to an associated PID capsule, as will be described hereinbelow.

When the assembled electrode contact pellet is snap-fitted to an associated PID capsule, the two further terminal pins thereof make contact with the respective ends of the contact strip extending between the two holes 14, 15, to confirm that the pellet is correctly fitted to the capsule.

Figure 4:
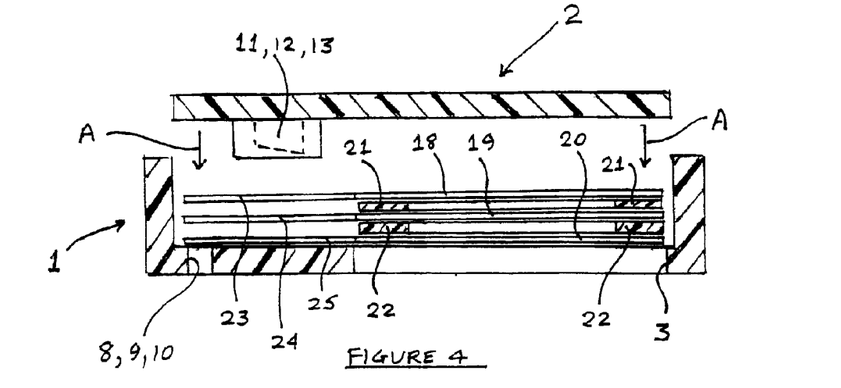
FIG. 4 is a diagrammatic, partial sectional elevation of the pellet of FIG. 1 in a partially-assembled condition.
Figure 5:
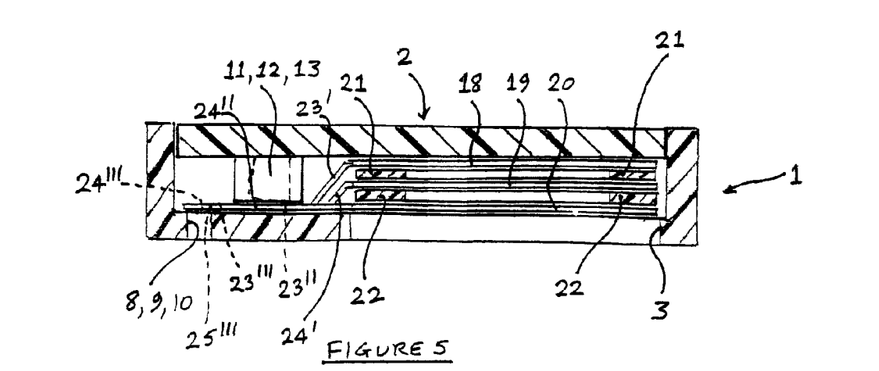
FIG. 5 is a diagrammatic, partial sectional elevation of the pellet shown in FIG. 4 but in its assembled condition.

On assembly of the pellet, as shown in FIGS. 4 and 5, three electrodes 18, 19, 20 and respective insulating annular spacers 21, 22 are located in the base body 1, such that their respective contacts, 23, 24, 25 lie, along with their respective electrodes 18, 19, 20, in spaced parallel planes, as shown in FIG. 4, with the respective free ends of the three contacts 23, 24, 25 overlying respective holes 8,9,10 in the base body 1.

The lid 2 is aligned with the open top (FIG. 4) of the base body 1, with the lid protrusions 11, 12, 13 depending downwardly in alignment with their respective electrode contacts 23, 24, 25.

It is to be appreciated that for reasons of clarity, the further holes 14, 15 in the base body 1 are not shown and, also, that FIGS. 4 and 5 are purely diagrammatic and not to scale.

Then, the lid 2 is fitted to the base body 1, as shown in FIG. 5, such that the lid protrusions 11, 12, 13 engage their respective electrode contacts 23, 24, 25, such that the upper two contacts 23, 24 are deformed downwardly into the plane of the lowermost electrode contact 25.

In the arrangement shown in FIG. 5, with the lid 2 fitted to the base body 1, the uppermost contact 23 in FIG. 4 now comprises a downwardly depending portion 23' and another portion 23" extending in the plane of the lowermost contact 25, with its free end portion 23''' overlying its respective hole 10 in the recess 7 of the base body 1. Similarly, a portion 24' of the electrode contact 24 (FIG. 4) depends downwardly, with a portion 24" also extending in the plane of the lowermost contact 25, with its free end portion 24''' overlying its respective hole 9 in the recess 6 of the base body 1.

In this manner, the two upper electrode contacts 23, 24 of FIG. 4 have been deformed downwardly, such that portions 23", 24" thereof lie in a common plane with the lowermost electrode contact 25 whose free end portion 25''' also overlies its respective hole 8 in the recess 5 of the base body 1.

The lid 2 is then secured firmly in position on the base body 1, for example, by ultrasonic welding or any other suitable means.

Figure 6:
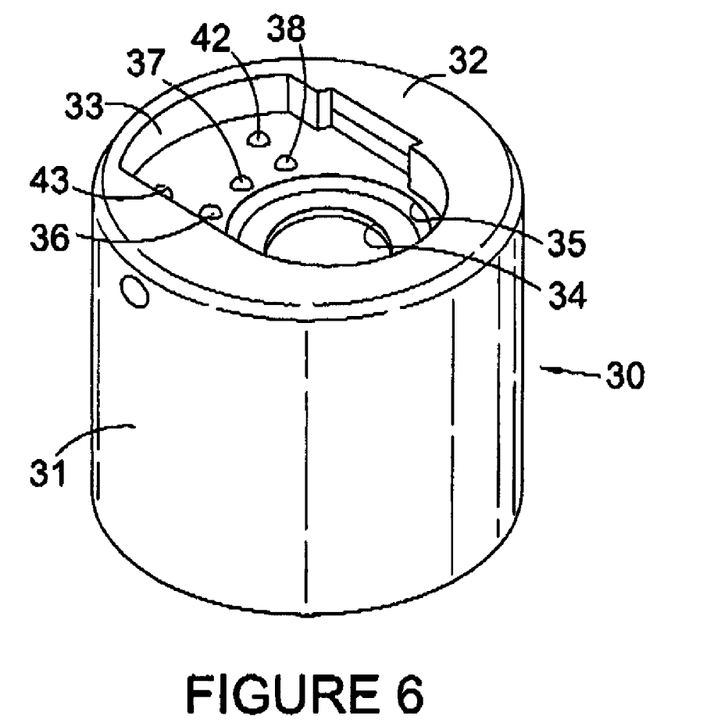
FIG. 6 is a perspective view of the body of a photoionisation detector capsule.
Figure 7:
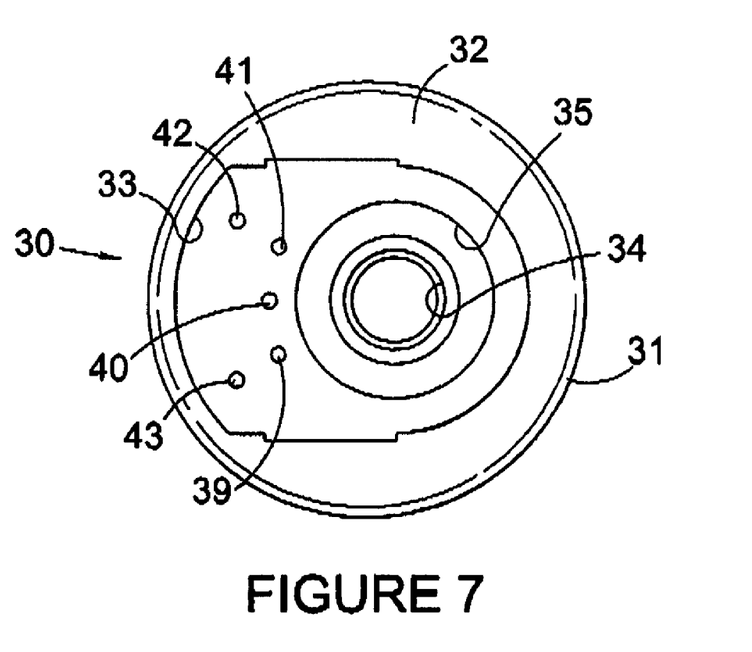
FIG. 7 is a plan view of the capsule shown in FIG. 6.

Thus, there is provided a compact integral pellet for subsequent fitment to a PID capsule, such as that generally designated 30 in FIGS. 6 and 7.

This PID capsule 30 comprises a generally cylindrical body 31 with a top 32 having a recess 33 whose shape and depth correspond generally with those of the pellet described above in relation to FIG. 5.

In the recess 33, there is provided a circular aperture 34 and associated annular recess 35 for receiving an ionisation lamp, as will be described below.

Also, the recess 33, as shown in FIG. 6, has three holes 36, 37, 38 through which are receivable respective fixed terminal pins 39, 40, 41 of equal height, as shown in FIG. 7, and which, when the pellet is assembled to the top 32 of the capsule body 31, lie in register with corresponding holes of the base body 1.

Similarly, the circular aperture 34 in the recess 33 of the top 32 of the capsule body 31 lies in register with the circular aperture 3 in the base body 1 of the assembled pellet.

Further, additional holes 42, 43 provided in the recess 33, as shown in FIG. 6, lie in register with corresponding holes 14,15 in the base body 1 of the pellet.

As shown in FIG. 7, these additional holes 42, 43 also receive therein additional fixed terminal pins for engaging a contact (not shown) extending between the holes 42, 43, which forms part of a circuit for determining the presence or absence of the assembled pellet with respect to the PID capsule 30.

Figure 8:
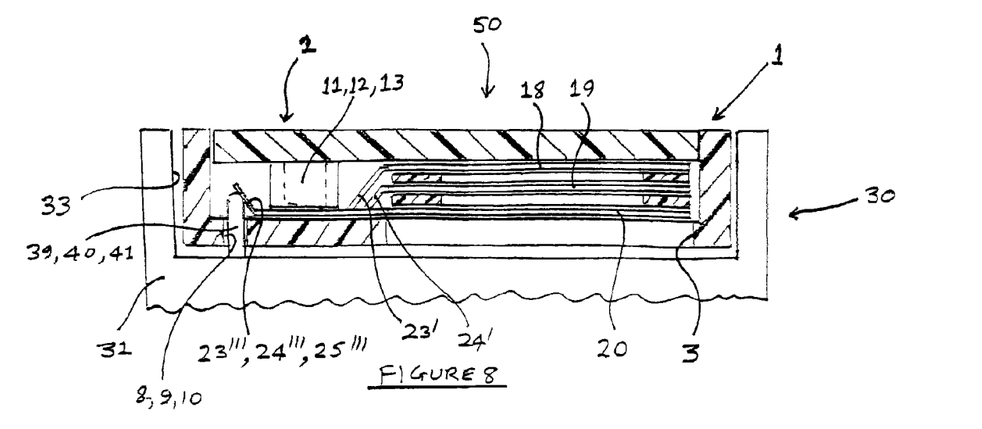
FIG. 8 is a diagrammatic, partial sectional elevation of the pellet of FIGS. 1 and 5 fitted to the capsule of FIGS. 6 and 7.

In FIG. 8, the assembled pellet, now indicated generally at 50, is shown fitted in the recess 33 of the top 32 of the PID capsule base 31. As the pellet 50 is fitted into that recess 33, the rounded ends of the terminal pins 39, 40, 41, which are of equal height and which extend through respective holes 36,37,38 in the recess 33, engage the free ends 23''', 24''', 25''' of the electrode contacts 23, 24, 25 with a scraping action, to provide good ohmic contact therebetween as the free contact ends 23''', 24''', 25''' are deformed in a direction opposite to that in which the contact portions 23', 24' extend.

In this manner, good ohmic contact is made between the circuitry associated with the PID capsule 30 and the electrode contacts and the electrodes 18, 19, 20 themselves.

Figure 9:
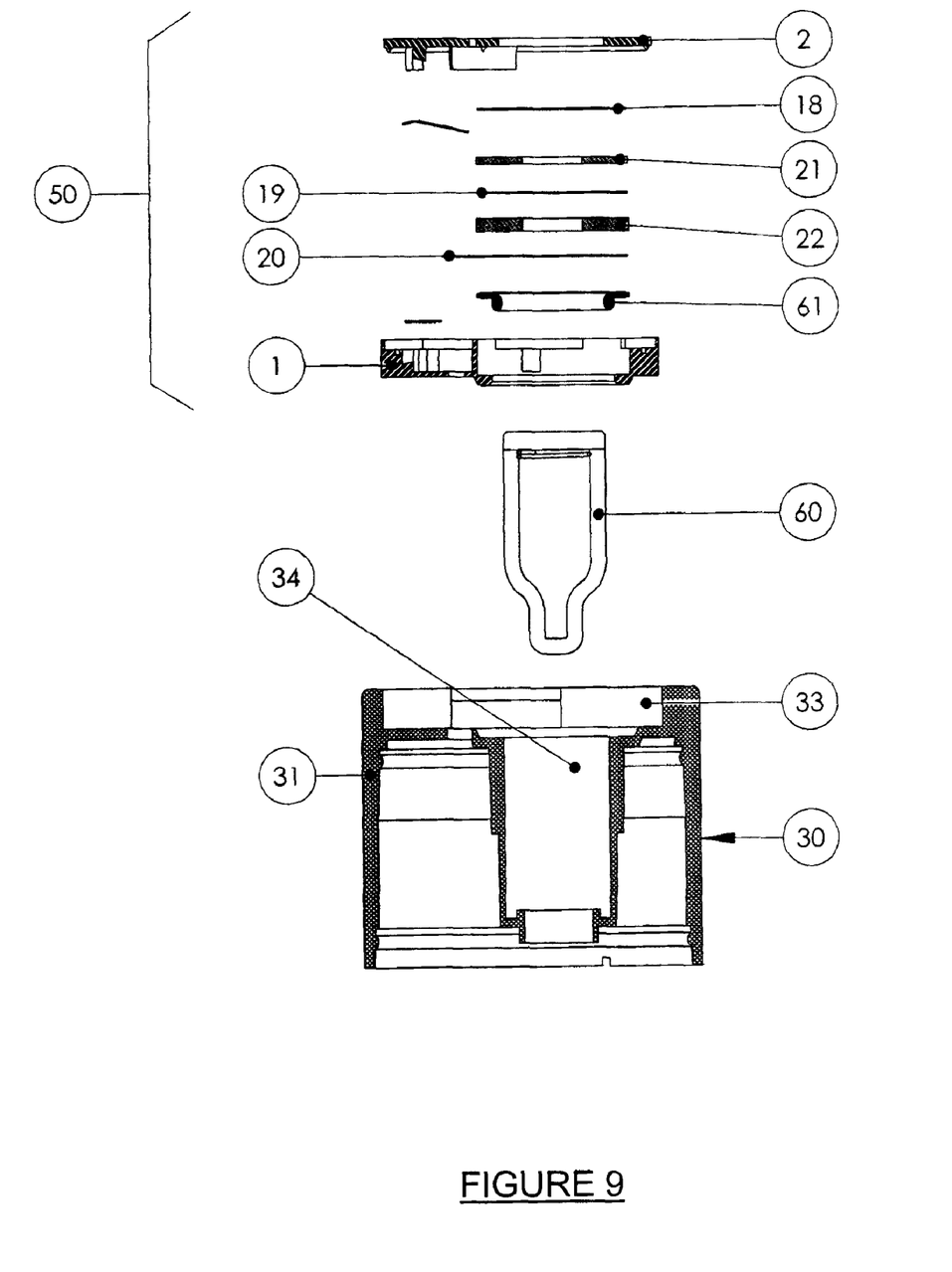
FIG. 9 is an exploded sectional elevation of the pellet of FIGS. 1 to 5 and the capsule of FIGS. 6 and 7 before assembly.

FIG. 9 illustrates an exploded sectional view of a PID assembly comprising the unassembled pellet 50 including the base body 1, lid 2, electrodes 18, 19, 20 and respective insulating spacers 21, 22. An ionisation lamp 60 and associated O-ring 61 for fitting into the PID capsule body 31 via the circular aperture 34 is also shown.

Figure 10:
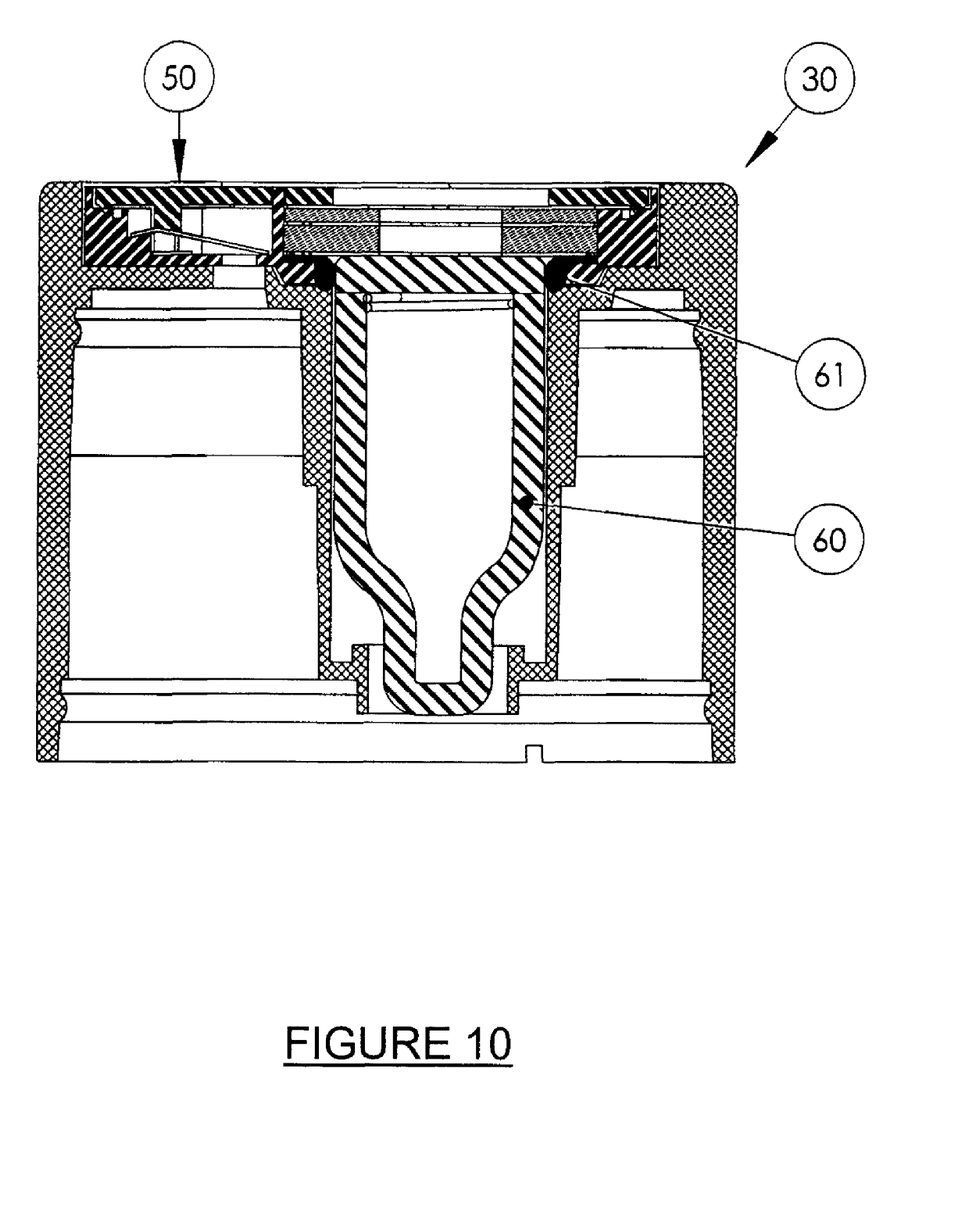
FIG. 10 is a sectional elevation of the pellet of FIGS. 1 to 5 assembled to the capsule of FIGS. 6 and 7.

FIG. 10 shows the assembled PID capsule 30 including the pellet 50, ionisation lamp 60 and O-ring 61.

Figure 11:
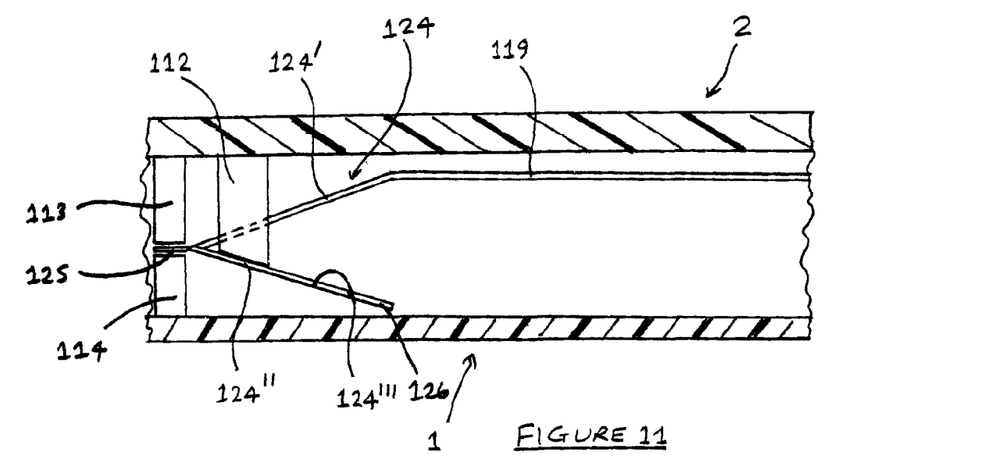
FIG. 11 is a diagrammatic, partial sectional elevation of an electrode pellet with an electrode contact, in an assembled condition of the pellet.
Figure 12:
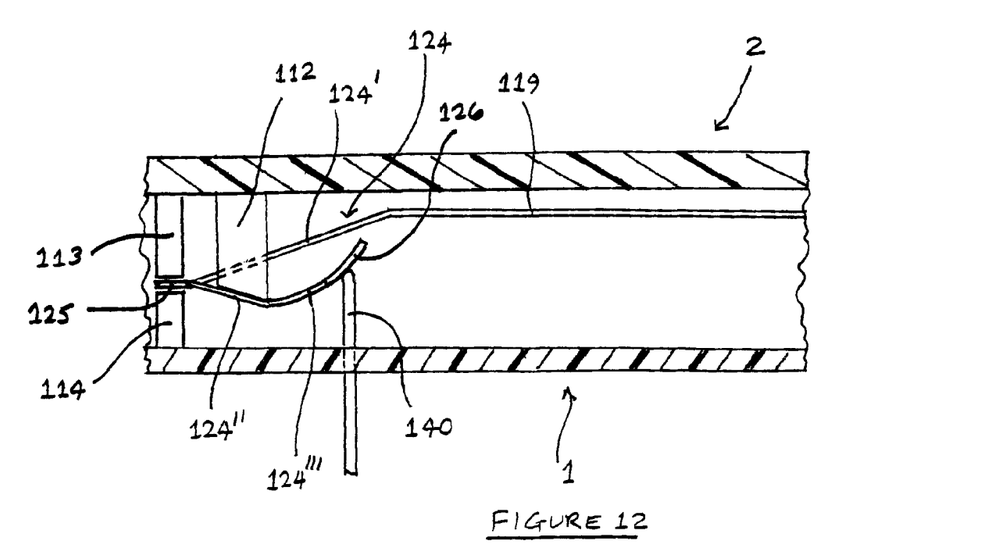
FIG. 12 is a diagrammatic, partial sectional elevation of the pellet of FIG. 12 in its assembled condition and with the electrode contact engaged by a terminal pin of a PID capsule.
Figure 13:
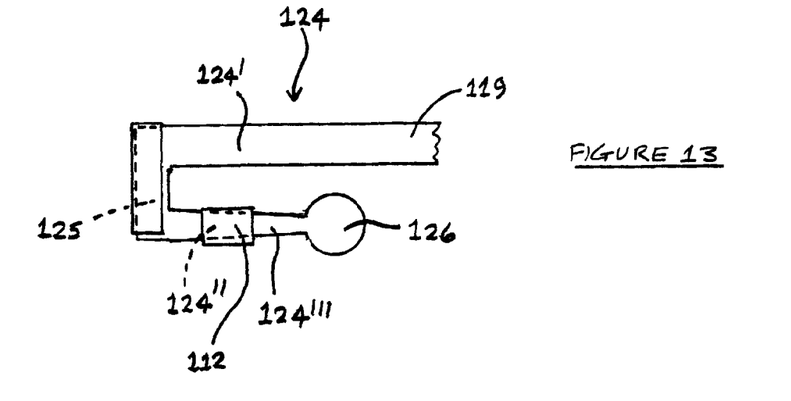
FIG. 13 is a plan view of part of the pellet shown in FIGS. 11 and 12, showing the electrode contact located therein.

Referring now to FIGS. 11, 12 and 13 of the drawings, here there is shown a modified electrode 119 and associated contact 124 arrangement. For reasons of clarity, the other electrodes and associated contacts are not shown in these two Figures.

As in the case of the three electrodes 18, 19, 20 and associated contacts 23, 24, 25 discussed above, before the pellet is assembled, for example as shown in FIG. 4, the electrode 119 and a first portion 124', an intermediate portion 124", a second portion 124''', a clamping portion 125 and a circular portion 126 of the contact 124 all lie in a common plane, with the portions 124", 124''' extending backwards with respect to and adjacent the portion 124' and connected integrally thereto by the clamping portion 125.

The base body 1 is provided with a protrusion 114, whilst the lid 2 has a corresponding protrusion 113.

On assembly of the pellet and when the lid 2 is applied to the base body 1, for example, as shown in FIG. 5, the lid protrusion 112 engages the portion 124" of the contact 124, thereby deforming downwardly the portion 124' and, to some extent, the portions 124", 124''', 125 of the contact, as shown in FIG. 11.

Also, the lid protrusion 113 engages the portion 125 of the contact 124, which portion 125 is also deformed downwardly to engage the base body protrusion 114, so that the contact portion 125 is effectively sandwiched between the lid and base body protrusions 113, 114.

Subsequently, and when the so-assembled pellet is applied to a PID capsule, such as that shown at 30 in FIGS. 6, 7 and 9, the corresponding terminal pin 140 (FIG. 12) of that capsule engages the circular portion 126 of the electrode contact 124 with its rounded end, to deform the portions 124''', 126 in a direction opposite to that in which the portion 126 extends. In this manner, the rounded end of the terminal pin 140 engages the portion 124''' with a scraping action, to provide good ohmic contact therebetween during such oppositely-directed deformation.

In this manner, the portion 125 of the contact 124 is sandwiched firmly between the lid and base body protrusions 113, 114, so that when the circular contact portion 126 is engaged by the terminal pin 140 of the PID capsule only the contact portions 124''', 126 are deformed by the terminal pin 140, without unwanted deformation of the remaining portions 124', 124", 125 of the contact 124 which might otherwise detract from the integrity of the components of the contact assembly.

Although the other electrodes and associated contacts are not shown in FIGS. 11 and 12, it is to be assumed that they are configured, prior to and during assembly of the pellet, as discussed above in relation to FIGS. 4, 5 and 8 and, subsequently, when fitted within a PID assembly, as also described above in relation to FIGS. 7, 9 and 10.

The invention is not limited to any particular configuration of electrodes.

As discussed above in relation to FIGS. 6 and 7, the electrodes can be configured to include a circuit determining or indicating correct installation of the assembled pellet on a photoionisation detector or other module.

Our granted patents EP 1474681 and U.S. Pat. No. 7,046, 012 describe and claim an ionisation detector including a third or fence electrode wherein, inter alia, current drawn from the fence electrode provides a measure of the degree of contamination or condensation within the detector and of lamp efficiency. Such electrode arrangement can advantageously be incorporated into the present invention.

It is to be appreciated that the invention provides a demountable and replaceable pellet and an associated pellet/PID capsule assembly which have distinct advantages over the prior art arrangements discussed above.

The electrode contacts are deformable in such a manner that when they are further deformed by engagement with the fixed terminal pins, they are scraped by the rounded ends of the terminal pins as they slide thereover, to remove oxide and other debris between the respective contact/terminal surfaces. This can be done in one action as the pellet is fitted into place upon the PID capsule.

Physical alignment is not crucial in any dimension but this sliding and scraping action of the terminal pins upon the flat surfaces of the electrode contacts is able to take-up movement and self-alignment in all three dimensions.

Also, costs are reduced to a minimum, in that there are only two parts, one part being the fixed terminal pins and the other being a mere extension contact of the associated electrode.

Environmental effects are also minimised, due to the wiping action discussed above. The pellet represents the disposable part of a PID capsule and can thus be inexpensively exchanged to retain original performance.

While the invention has been described with reference to photoionisation detectors, it is applicable to other demountable electrode assemblies.

Other manufacturing benefits are forthcoming from this invention.

First, the electrodes require no further manufacturing processes to cause permanent deformation prior to their being loaded into the pellet, thus saving on separate inventory control and additional tooling.

Second, because the electrodes of the pellet are assembled in their flat, undeformed state, visual inspection is readily accessible to identify rogue parts which is more difficult to achieve with preformed components.

Third, flat electrodes are much more easily loadable into the pellet, preformed components being more likely to tangle when together, technically called "fish-hooking".

Fourth, two of the electrodes can be designed to be mirror images. Thus, the same electrodes may be placed within the pellet because the pellet body during assembly creates the left-hand part and right-hand part simultaneously in the one closing action.

The invention claimed is:

1. A demountable pellet for use as an electrode contact assembly in a photoionisation detector, comprising:
    a base upon which is mounted a plurality of electrodes arranged in respective spaced parallel planes and having respective contacts protruding therefrom, and a closure for the base having a member engaging at least one of the electrode contacts,
    wherein, in an unassembled condition of the pellet, with the closure separate from the base and the at least one closure member disengaged from its respective electrode contact, the contacts lie in respective spaced parallel planes and
    wherein, in the assembled condition of the pellet with the least one closure member engaging its respective electrode contact, at least one of the contacts lies in a plane other than that in which it lay in the unassembled condition of the pellet, and wherein, in the assembled condition of the pellet, each electrode contact overlies a corresponding hole through which respective fixed terminal pins are receivable from the exterior of the pellet to provide ohmic contact therebetween, and wherein, in the assembled condition, all the electrode contacts lie in a common plane, and wherein the demountable pellet engages mechanically and electrically with the photoionisation detector.

2. A pellet as claimed in claim 1 wherein the holes are provided in a wall of the pellet base.

3. A pellet as claimed in claim 1 wherein each electrode contact extends into a corresponding recess overlying the corresponding hole.

4. A pellet as claimed in claim 1 wherein the fixed terminal pins are of substantially the same height.

5. A pellet as claimed in claim 1 wherein the base includes a circular aperture for alignment with one end of an ionisation lamp.

6. A pellet as claimed in claim 1 wherein the electrodes are configured to include a circuit determining or indicating correct installation of the assembled pellet on the photoionisation detector.

7. A pellet as claimed in claim 1 wherein at least one electrode is configured to receive current drawn from a fence electrode associated with a corresponding ionisation detector, which current provides a measure of at least one of the degree of contamination or condensation within the detector and of lamp efficiency.

8. A photoionisation detector capsule incorporating a demountable pellet for use as an electrode contact assembly in a photoionisation detector, which pellet comprises:
    a base upon which is mounted a plurality of electrodes arranged in respective spaced parallel planes and having respective contacts protruding therefrom, and a closure for the base having a member engaging at least one of the electrode contacts,
    wherein, in an unassembled condition of the pellet, with the closure separate from the base and the at least one closure member disengaged from its respective electrode contact, the contacts lie in respective spaced parallel planes and
    wherein, in the assembled condition of the pellet with the at least one closure member engaging its respective electrode contact, at least one of the contacts lies in a plane other than that in which it lay in the unassembled condition of the pellet, and
    wherein each electrode contact overlies a corresponding hole through which respective fixed terminal pins are receivable from the exterior of the pellet to provide ohmic contact therebetween, and
    wherein, in the assembled condition, all the electrode contacts lie in a common plane, and
    wherein the demountable pellet engages mechanically and electrically with the photoionisation detector.

9. A demountable pellet for use as an electrode contact assembly in a photoionisation detector, comprising:
    a base upon which is mounted a plurality of electrodes arranged in respective spaced parallel planes and having respective contacts protruding therefrom, and a closure for the base having a member engaging at least one of the electrode contacts,
    wherein, in an unassembled condition of the pellet, with the closure separate from the base and the at least one closure member disengaged from its respective electrode contact, the contacts lie in respective spaced parallel planes and
    wherein, in the assembled condition of the pellet with the least one closure member engaging its respective electrode contact,
    (a) at least one of the contacts lies in a plane other than that in which it lay in the unassembled condition of the pellet and wherein each electrode contact overlies a corresponding hole through which respective fixed terminal pins are receivable from the exterior of the pellet to provide ohmic contact therebetween, and
    (b) at least one of the electrode contacts includes at least one portion at an angle to an adjacent portion, and (c) wherein, in the assembled condition, all the electrode contacts lie in a common plane, and (d) wherein the demountable pellet engages mechanically and electrically with the photoionisation detector.

10. A pellet as claimed in claim 9 wherein the said at least one electrode contact comprises a first portion connected through an integral clamping portion to an intermediate portion and a second portion, wherein the intermediate and second portions extend backwards with respect to and adjacent the first portion.

11. A pellet as claimed in claim 10 additionally including a closure member engaging with said integral clamping portion.

12. A pellet as claimed in claim 11 additionally including protrusions from the base corresponding with the respective closure members.

13. A pellet as claimed in claim 9 wherein the base includes a circular aperture for alignment with one end of an ionisation lamp.

14. A pellet as claimed in claim 9 wherein the electrodes are configured to include a circuit determining or indicating correct installation of the assembled pellet on the photoionisation detector.

15. A pellet as claimed in claim 9 wherein at least one electrode is configured to receive current drawn from a fence electrode associated with a corresponding ionisation detector, which current provides a measure of at least one of the degree of contamination or condensation within the detector and of lamp efficiency.

16. A method of assembling a pellet for use as a demountable electrode contact assembly in a photoionisation detector, which method comprises:

providing a base upon which is mounted a plurality of electrodes arranged in respective spaced parallel planes and having respective contacts which protrude therefrom and lie in respective spaced parallel planes;

providing a closure having at least one member for engaging one or more of the electrode contacts when the closure is fitted to the base; and fitting the closure to the base, to cause the at least one closure member to engage its electrode contact and to deform the said electrode contact into a plane other than that in which it lay prior to the closure being fitted to the base, wherein each electrode contact overlies a corresponding hole through which respective fixed terminal pins are receivable from the exterior of the pellet to provide ohmic contact therebetween, and wherein, in the assembled condition, all the electrode contacts lie in a common plane, and wherein the demountable pellet engages mechanically and electrically with the photoionisation detector.

* * * * *